United States Patent [19]

Calzi et al.

[11] Patent Number: 5,244,561
[45] Date of Patent: Sep. 14, 1993

[54] PROCESS AND APPARATUS FOR THE ELECTROCHEMICAL DETERMINATION OF $pCO_2$ IN BLOOD

[75] Inventors: Claudio Calzi; Gabrio Tancredi, both of Milan, Italy

[73] Assignee: Instrumentation Laboratory S.R.L., Milan, Italy

[21] Appl. No.: 756,566

[22] Filed: Sep. 11, 1991

[30] Foreign Application Priority Data

Sep. 14, 1990 [IT] Italy ............................... 21475 A/90

[51] Int. Cl.$^5$ ........................................... G01N 27/26
[52] U.S. Cl. ................................. 204/415; 204/409; 204/403; 204/153.17; 422/82.02; 422/82.03; 436/66
[58] Field of Search .................... 422/82.02, 82.03; 436/66; 204/403, 409, 415, 153.17

[56] References Cited

U.S. PATENT DOCUMENTS

| | | | |
|---|---|---|---|
| 3,926,561 | 12/1975 | Lucero | 436/175 |
| 3,960,498 | 6/1976 | Zindler et al. | 204/411 |
| 4,197,853 | 4/1980 | Parker | 204/412 |
| 4,490,234 | 12/1984 | Buzza | 204/409 |

Primary Examiner—John Niebling
Assistant Examiner—Bruce F. Bell
Attorney, Agent, or Firm—Testa, Hurwitz & Thibeault

[57] ABSTRACT

In a blood gas analyzer, a measurement liquid, advantageously high-purity water, is fed from a suitable vessel to a diffusion cell in which the measurement liquid is brought into contact via a diffusion membrane with the blood sample to be tested. When the gases dissolved in the sample have diffused through the membrane, the measurement liquid which has remained static in the diffusion cell is propelled into a measuring cell in which the value of an electrical quantity related to the $pCO_2$ is determined. The measurement liquid is then fed to discharge. In a preferred embodiment, the measurement liquid is discharged into the vessel from which it has been initially withdrawn via passage through means for retaining ionic impurities.

18 Claims, 3 Drawing Sheets

PROCESS AND APPARATUS FOR THE ELECTROCHEMICAL DETERMINATION OF PCO₂ IN BLOOD

DESCRIPTION

This invention relates to improvements in the electrochemical determination of gaseous or volatile species, in particular the blood partial pressure of $CO_2$ in a blood gas analyzer. General problems relating to the maintenance and calibration of blood gas instruments are discussed in the introduction of patent applications EP-A-0354604 and EP-A 0358250.

The object of the present invention is to provide a system suitable for the electrochemical determinations of the carbon dioxide partial pressure in a blood sample which overcomes the typical drawbacks of known apparatus and processes, so providing high reliability and requiring practically no ordinary maintenance, but without leading to any appreciable fall-off in the apparatus performance between the programmed shutdowns for replacing those parts of the apparatus which by their nature have a limited life.

A particular object of the invention is to restore the apparatus to constant controlled conditions after each measurement, this expedient being considered essential for obtaining reproducible and reliable measurements.

A further object of the invention is to enable the proper operation of the entire apparatus to be checked simply by checking the time interval between the successive measurement on the various samples.

SUMMARY OF THE INVENTION

To this end the invention provides a process for obtaining the value of an electrical quantity related to the $pCO_2$ in a blood sample, comprising:
a) withdrawing from a suitable vessel a measurement liquid maintained under high-purity conditions by passage through means for retaining ionic impurities;
b) propelling said liquid as far as a diffusion cell in which it is brought into contact with the blood sample via a permeation membrane which allows only gases to diffuse;
c) halting the flow of measurement liquid to allow the dissolved gases to diffuse through the membrane between the sample and the quantity of measurement liquid contained in the diffusion cell;
d) propelling the measurement liquid so that the quantity of measurement liquid which has remained static in the diffusion cell flows into a measuring cell, then measuring in this quantity of liquid the value of an electrical quantity related to the $pCO_2$; and
e) feeding the measurement liquid to discharge when the electrical measurement has been effected.

The apparatus according to the invention comprises a fluid circuit which starts from a measurement liquid vessel with which means for retaining ionic impurities are associated, and passes in succession through a diffusion cell in which the path of said liquid is separated by a permeation membrane from a path which receives a blood sample, and a measuring cell comprising means for providing the value of an electrical quantity related to the $pCO_2$ of said measurement liquid, the circuit terminating at discharge; means also being provided for propelling said measurement liquid into said fluid path. Certain aspects of the present method and apparatus are found in U.S. Pat. No. 4,209,299 which employs a conductivity measurement to determine dissolved carbon dioxide in serum or plasma, a quantity different from $pCO_2$ in blood.

Italian application 21292 A/88 filed Jul. 8, 1988 (EP-A-0354604) discloses a process for measuring carbon dioxide in a biological sample with the sample stopped on one side of a membrane in a diffusion cell. Electrolyte in the other side of the membrane is also stopped, but later flows from the diffusion cell to a pH electrode. This reference does not indicate whether the sample is blood, serum or a mixture of serum with acid to liberate dissolved carbon dioxide.

BRIEF DESCRIPTION OF THE DRAWING

The objects and characteristics of the present invention will be more apparent from the description of a non-limiting embodiment thereof given hereinafter with reference to the accompanying drawings, in which.

DETAILED DESCRIPTION

Figure 1:
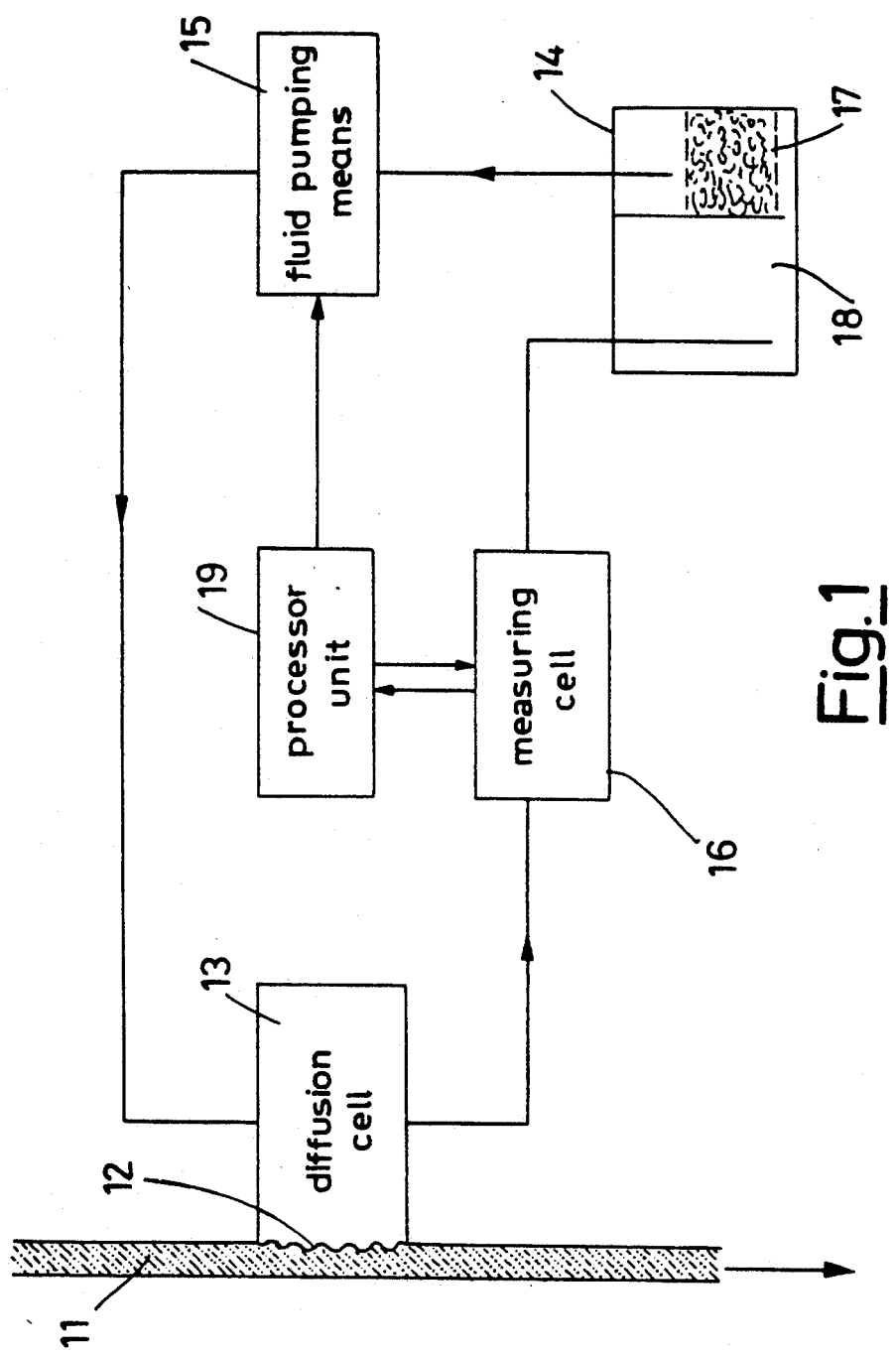
FIG. 1 is a general schematic view of an embodiment of the apparatus according to the invention.

The apparatus shown in FIG. 1 comprises a duct 11 to receive the blood sample of which the $pCO_2$ is to be measured, and communicating via permeation membrane 12 with a diffusion cell 13 forming part of a closed fluid circuit through which a measurement liquid is circulated. This circuit also comprises a vessel 14 containing the measurement liquid, fluid pumping means 15, and a measuring cell 16.

Examining the components of the apparatus in detail, the fluid pumping means 15 can consist of metering pumps of known types for feeding controlled quantities of measurement liquid into the circuit to enable predetermined quantities of liquid to selectively reach the various units provided in the circuit.

Such metering pump 15 can be totally controlled by a data processing unit 19 which implements the sequential execution of the operations required by the measurement process by sequentially operating the means provided for this purpose, such as the pumping unit 15 and the sensors of the measuring cell 16. The unit 19 also processes the data received from the sensors of the measuring cell 16 and controls or enables the various sequential operations while at the same time handling the various measurements. The processing unit 19 will not be further described as it can be constructed in various known ways.

The vessel 14 is divided into two compartments, namely a first treatment compartment 17 from which the measurement liquid is withdrawn substantially free of ionic impurities to be fed into the fluid circuit, and a second compartment 18 for collecting the solution originating from the measuring cell 16 when measurement of the contained $CO_2$ has been effected. The partition dividing compartments 17 and 18 stops before reaching the bottom of vessel 14, thereby leaving an opening through which liquid can flow from compartment 18 into compartment 17.

Ion exchangers in mixed bed form (cationic and anionic) are provided in the compartment 17 for maintaining the quality of the measurement liquid used.

The measuring cell 16 is advantageously a conductivity cell, for example of thin layer type, although conductivity cells of any known type can be used.

The diffusion cell 13 is to be considered a totally known unit in terms of its concept, in that it is merely required to bring the measurement solution into contact with the sample flowing through the duct 11, via a permeation membrane which allows gases to diffuse between the two liquids but does not allow ions to pass.

The measurement process using the described apparatus is conducted in the following manner. When the sample to be analyzed is introduced into the duct 11, the pump 15 feeds a quantity of measurement liquid into the fluid circuit and hence into the diffusion cell 13. It should be noted that during this stage in which the measurement liquid is being fed into the diffusion cell 13 the measuring cell 16 can be used to verify the suitability of said liquid for its required purpose. In this respect, any contamination of the liquid, or indeed any accidental lack of liquid, would be immediately signalled as a warning of the impossibility of effecting the measurement which is to be made. The processing unit 19 reacts in the sense of blocking the analysis procedure if it receives abnormal signals from the cell 16 during this stage.

The instrument can be suitably calibrated to compensate for that $pCO_2$ of the measurement liquid deriving from the percentage of $CO_2$ present in the atmosphere, which however is know to be very small (around 0.03%) and therefore such as not to appreciably influence the measurement.

When a quantity of measurement liquid has reached the diffusion cell 13, the flow is halted for a determined time. $CO_2$ necessarily diffuses from the sample to the measurement liquid, this diffusion being a function of the $pCO_2$ in the sample and the time for which the two fluids remain in contact via the membrane 12.

Figure 2:
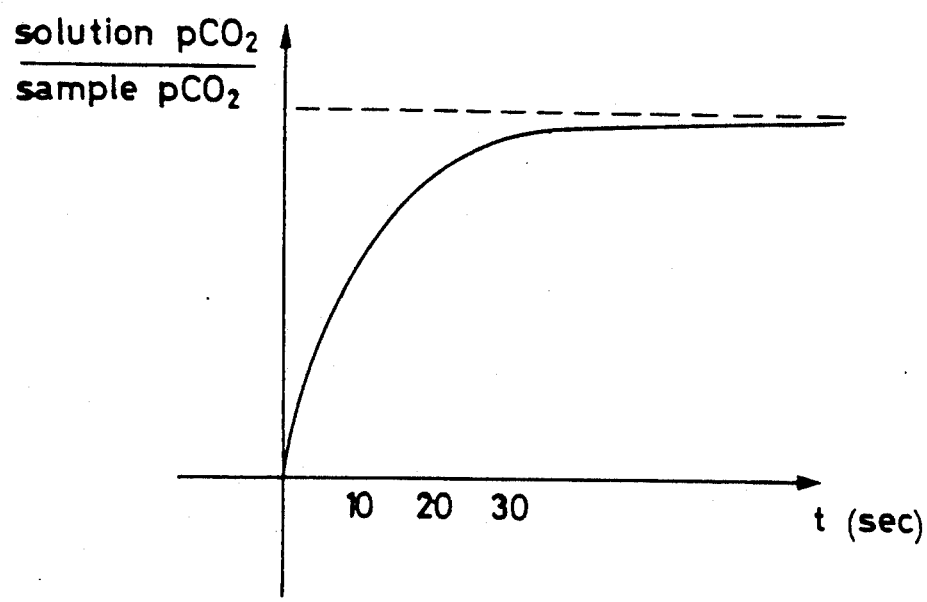
FIG. 2 and FIG. 3 are graphs showing the variation in certain parameters measured in the system of FIG. 1.

The diagram of FIG. 2 shows how the $pCO_2$ in the solution can be considered to vary qualitatively as a function of the sample $pCO_2$ and as a function of time. The vertical axis represents the ratio of solution $pCO_2$ to sample $pCO_2$ and the horizontal axis represents time. For measurement accuracy, and as time is not a critical factor, the measurement solution is retained in the diffusion cell until the derivative of the function shown in FIG. 2 reaches a value sufficiently low to allow the usual variations in residence time to be considered negligible. For example, in general a residence time of 20 seconds can be considered sufficient, as a compromise between measurement accuracy and measurement speed. On termination of the permeation stage, the pump 15 pumps the measurement liquid so that the quantity held in the diffusion cell 13 flows into the measuring cell 16, which dynamically provides an electrical signal, in the form of a peak, containing the information relative to the sample $pCO_2$.

The present measuring cell 16 therefore forms part of a flow system in which a signal related to the partial pressure of the carbon dioxide contained in the test blood sample undergoes dynamic conductimetric measurement.

Figure 3:
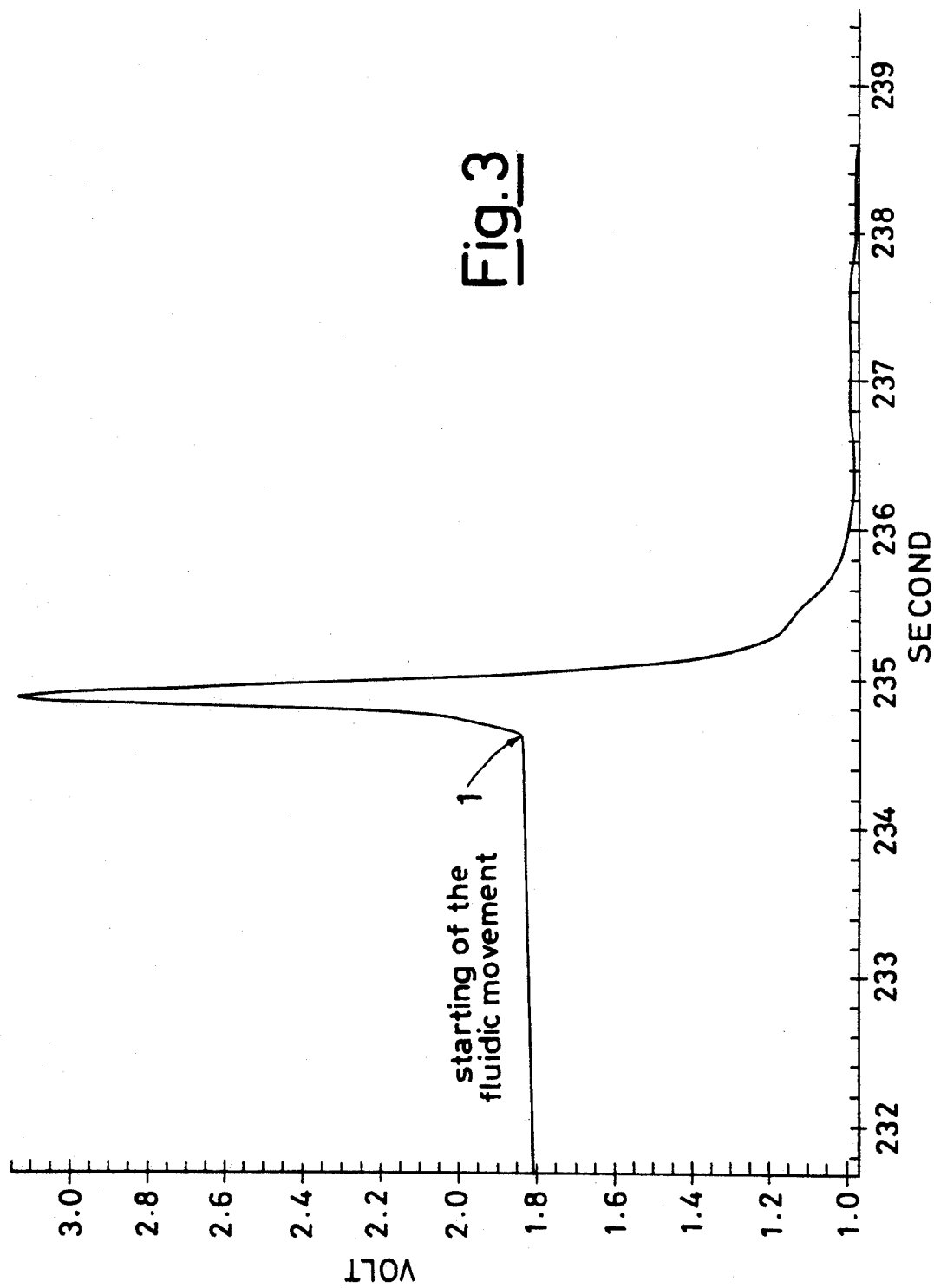

To indicate qualitatively the type of signal which can be emitted by the conductivity cell 16, FIG. 3 shows a typical signal pattern during solution flow, which can be arrested after the peak has been measured. The qualitative variation in the signal emitted by the measuring cell can be of the type shown in FIG. 3.

In the specific case of $CO_2$ the measurement liquid consists advantageously of high-purity water. The use of any compound or solution with which the diffused species established acid/base equilibrium with consequent production of ions responsible for electrical conductivity variation is however also possible.

The maximum deviation of the measured dynamic signal from its initial value before fluid movement is preferably but not exclusively used to relate the conductivity change to the sample $pCO_2$. The processor unit automatically makes the calculations required to obtain the $pCO_2$ value of the sample.

The time within which the peak value is reached represents substantially an instrument constant and is therefore of diagnostic interest with regard to the correct operation of the instrument. In this respect, such quantification of the measurement time and the related quantification of the fluid movements within the fluid circuit makes it possible to check whether or not the entire apparatus is operating correctly, thus providing an operational check for the device on the basis of time.

Having executed the measurement, the processing unit 19 causes the measurement liquid to be fed to the vessel 14 where it is eluted through an ion exchanger bed contained in 17 to be then withdrawn for the next measurement. Such ion exchangers are advantageously in mixed bed form and in particular are in the form of ion exchange resins, although inorganic ion exchangers can also be used. Such ion exchangers can be used in granular, liquid or membrane form. One example of a suitable resin is Duolite MB 6113 produced by the firm BDH; other examples are resins (with trademark owner in parenthesis):

Amberlite MB-1 (Rohm and Haas)
Biodeminrolit (Dia-prosim)
Zerolit DM-F (Zerolit)
AG501-X8 (Biorad)

Examples of suitable inorganic ion exchangers are zeolites.

It is important to note that with the apparatus according to the invention, using the described method of operation, the particular object of the invention can be attained: to restore the initial conditions with absolute precision after every measurement, this being essential for measurement repeatability.

In this respect, on beginning a new measurement, the pump 15 pumps the measurement liquid as far as the diffusion cell 13, thus at the same time propelling the solution contained in the circuit into the vessel 14, and allowing a check to be made in the measuring cell that a measurement liquid with the required physical and chemical characteristics is effectively flowing through the current.

We claim:

1. A process for determining $pCO_2$ in a blood sample, comprising:

a) withdrawing a measurement liquid which is free or close to free of ionic impurities from a vessel, wherein said liquid is rendered free or close to ion-free in said vessel by passage through means for removing ionic impurities;

b) propelling said liquid to a diffusion cell in which it is brought into contact with the blood sample via a permeation membrane which is permeable to gases but not to ions;

c) halting the flow of measurement liquid for a time sufficient to allow the gases to diffuse through the membrane between the sample and the measurement liquid contained in the diffusion cell;

d) propelling the measurement liquid into a measuring cell, and therein measuring the value of an electrical quantity related to the $pCO_2$ in said liquid; and e) discharging the measurement liquid.

2. The process of claim 1, wherein the measurement liquid is discharged into said vessel, so forming a closed fluid cycle.

3. The process of claim 1, wherein the measurement liquid is high-purity water.

4. The process of claim 1, wherein the measuring cell is a conductivity cell.

5. The process of claim 4, wherein the conductivity cell is of the thin layer type.

6. The process of claim 1, wherein the means of removing ionic impurities are ion exchangers.

7. The process of 6, wherein the ion exchangers are in mixed bed form.

8. The process of claim 7, wherein the ion exchangers in mixed bed form are ion exchange resins.

9. The process of claim 7, wherein the ion exchangers in mixed bed form are inorganic.

10. An apparatus for determining $pCO_2$ in a blood sample, comprising a
   a vessel containing means for removing ionic impurities from a measurement liquid,
   a diffusion cell located downstream of said vessel, in which said liquid is brought into contact with a blood sample via a permeation membrane which is permeable to gases but not to ions,
   a measuring cell located downstream of said diffusion cell, wherein the value of an electrical quantity related to the $pCO_2$ of the liquid passing through the cell is measured, and
   pump means located downstream of said vessel, for withdrawing the measurement liquid from the vessel and for propelling it along a fluid circuit formed by the vessel, the diffusion cell, and the measuring cell.

11. The apparatus of claim 10, wherein the measuring liquid is discharged into said vessel, thereby forming a closed fluid circuit.

12. The apparatus of claim 10, wherein the measurement liquid is high-purity water.

13. The apparatus of claim 10, wherein the measuring cell is a conductivity cell.

14. The apparatus of claim 13, wherein the conductivity cell is of the thin layer type.

15. The apparatus as claimed in claim 10, wherein the means for removing ionic impurities are ion exchangers.

16. The apparatus of claim 10, wherein the ion exchangers are in mixed bed form.

17. The apparatus of claim 16, wherein the ion exchangers in mixed bed form are ion exchange resins.

18. The apparatus of claim 16, wherein the ion exchangers in mixed bed form are inorganic.

* * * * *